(12) United States Patent
Xie et al.

(10) Patent No.: US 11,572,628 B2
(45) Date of Patent: Feb. 7, 2023

(54) PROCESS AND METHOD FOR REDUCING METAL CORROSION IN WATER

(71) Applicant: ECOLAB USA INC., St. Paul, MN (US)

(72) Inventors: Yanjiao Xie, Aurora, IL (US); Jothibasu Seetharaman, Pune (IN); James Joseph Michels, Naperville, IL (US); Frederick Swiecinski, Algonquin, IL (US); Donald A. Johnson, Batavia, IL (US); Pradeep Cheruku, Bolingbrook, IL (US)

(73) Assignee: ECOLAB USA INC., St. Paul, MN (US)

( * ) Notice: Subject to any disclaimer, the term of this patent is extended or adjusted under 35 U.S.C. 154(b) by 115 days.

(21) Appl. No.: 16/235,043

(22) Filed: Dec. 28, 2018

(65) Prior Publication Data

US 2019/0203362 A1    Jul. 4, 2019

Related U.S. Application Data

(60) Provisional application No. 62/613,255, filed on Jan. 3, 2018.

(51) Int. Cl.
*C23F 11/14* (2006.01)
*C07D 235/12* (2006.01)

(52) U.S. Cl.
CPC .......... *C23F 11/149* (2013.01); *C07D 235/12* (2013.01)

(58) Field of Classification Search
CPC ...... C23F 11/149; C23F 11/10; C07D 235/12; C02F 5/125; C02F 2303/08
See application file for complete search history.

(56) References Cited

U.S. PATENT DOCUMENTS 2,876,233 A * 3/1959 Keller .................. C07D 235/08
548/304.4
3,929,705 A * 12/1975 Minieri ................ C07D 235/06
523/122

(Continued)

FOREIGN PATENT DOCUMENTS

CN          1424435 A    6/2003
CN       100371499 C    2/2008

(Continued)

OTHER PUBLICATIONS

Piggott, Brian et al., "Copper Complexes of 2-α-Hydroxybenzimidazole (HL) and the Crystal and Molecule Structures of [Cu(HL)$_2$(NCS)$_2$] · 2Me$_2$CO and [Cu$_2$(HL)$_2$(L)$_2$(NO$_3$)$_2$] · 4Me$_2$SO" Polyhedron (1989) 8(6): 769-774.

(Continued)

*Primary Examiner* — Pamela H Weiss
(74) *Attorney, Agent, or Firm* — Eric D. Babych; Barnes & Thornburg LLP

(57) ABSTRACT

This disclosure relates to compositions and methods of reducing corrosion using benzimidazoles. The method may include adding a benzimidazole and a halogen to an aqueous system that is in contact with a metal surface. The halogen may be bromine, iodine, or any combination thereof. In some cases, adding the halogen may be optional depending on the substituents on the benzimidazole ring. Compositions are also disclosed that include a benzimidazole, optionally a halogen depending on the substituents on the benzimidazole ring, and optionally a halogen stabilizer.

9 Claims, 1 Drawing Sheet

(56) References Cited

U.S. PATENT DOCUMENTS

| | | | | |
|---|---|---|---|---|
| 4,395,294 | A | * | 7/1983 | Hobbins ............... C23F 11/149 106/14.16 |
| 4,818,413 | A | | 4/1989 | Hoover et al. |
| 5,128,065 | A | * | 7/1992 | Hollander ............... C23F 11/10 210/696 |
| 5,165,344 | A | | 11/1992 | Matsumoto et al. |
| 5,173,130 | A | * | 12/1992 | Kinoshita .......... B23K 35/3615 106/14.15 |
| 5,362,334 | A | * | 11/1994 | Adams ............... B23K 35/3615 106/14.16 |
| 5,411,677 | A | * | 5/1995 | Pickering ................ C23F 11/04 106/14.44 |
| 5,658,611 | A | * | 8/1997 | Ishido ..................... C23C 22/52 205/196 |
| 5,735,973 | A | * | 4/1998 | Sasahara ............... C23F 11/149 106/14.16 |
| 5,772,919 | A | | 6/1998 | Reichgott et al. |
| 5,773,627 | A | | 6/1998 | Anderson et al. |
| 5,968,408 | A | | 10/1999 | Anderson et al. |
| 6,103,144 | A | * | 8/2000 | Cheng ................... C23F 11/149 252/394 |
| 6,228,100 | B1 | * | 5/2001 | Schraga ............. A61B 5/15146 606/183 |
| 6,348,440 | B1 | * | 2/2002 | Meskers, Jr. .......... C11D 1/002 510/253 |
| 6,379,720 | B1 | * | 4/2002 | Cooper ................. A01N 65/08 424/94.1 |
| 6,524,644 | B1 | * | 2/2003 | Wengenroth ............. B23K 1/20 427/96.2 |
| 7,195,782 | B2 | * | 3/2007 | Moore ................... A01N 59/00 424/703 |
| 2003/0017693 | A1 | | 1/2003 | Han |
| 2003/0035749 | A1 | * | 2/2003 | Hann ..................... C23F 11/10 422/16 |
| 2003/0141351 | A1 | | 7/2003 | Akaike et al. |
| 2005/0173678 | A1 | | 8/2005 | Miura et al. |
| 2006/0014756 | A1 | * | 1/2006 | Edwards ................... A61P 9/10 514/254.06 |
| 2006/0199852 | A1 | * | 9/2006 | Iera ...................... C07D 263/57 514/375 |
| 2010/0291303 | A1 | * | 11/2010 | Abys ...................... C23F 11/10 427/343 |
| 2015/0152329 | A1 | * | 6/2015 | Seetharaman ......... C23F 11/149 548/254 |
| 2016/0177170 | A1 | * | 6/2016 | Janak ....................... C09K 8/54 507/242 |
| 2016/0348251 | A1 | | 12/2016 | Seetharaman et al. |
| 2016/0348252 | A1 | * | 12/2016 | Rane ..................... C23F 11/184 |
| 2017/0088523 | A1 | * | 3/2017 | Dixon ................ A61K 31/4196 |
| 2017/0107460 | A1 | | 4/2017 | Liu et al. |

FOREIGN PATENT DOCUMENTS

| | | | | |
|---|---|---|---|---|
| CN | 102121108 | A | 7/2011 | |
| CN | 102504364 | A | 6/2012 | |
| CN | 103436888 | A | 12/2013 | |
| CN | 106226991 | A | 12/2016 | |
| EP | 0508953 | A1 * | 10/1992 | ............... C02F 5/14 |
| GB | 782039 | A | 8/1957 | |
| KR | 20150084264 | A | 7/2015 | |
| RU | 1783796 | A1 | 4/1998 | |
| RU | 1382042 | A1 | 8/1998 | |
| RU | 2453632 | C2 | 6/2012 | |
| WO | WO 2007/007945 | A1 | 1/2007 | |
| WO | WO 2016/191672 | A1 | 12/2016 | |
| WO | WO 2016/191667 | A2 | 5/2017 | |
| WO | WO 2018/211450 | A1 | 11/2018 | |

OTHER PUBLICATIONS

Given, K.M. et al., "A New Halogen Resistant Azole(HRA) For Copper Corrosion Inhibition", BetzDearborn, 5 pages.

Holm, R. et al., "Chlorine's Effects on Triazole Inhibitor Layers on Copper", Environmental Effects, May 1994, 5 pages.

Holm, R. et al., The Impact of Chorine on Tolyltriazole and Butylbenzotriazole , Corrosion Inhibitor Films on Copper, International Water Conference 1992, Paper IWC-92-40, 19 pages.

Hu, Lian-Yue et al., "Corrosion Inhibition and Adsorption Behavior of Benzimidazole on Brass in 3% NaCl Solution", Corrosion Science and Protection Technology/Fushi Kexue yu Fanghu Jishu vol. 23, Iss. 4, (Jul. 2011): pp. 338-341.

Lu, F. et al., "Effect of Halogenation on Yellow Metal Corrosion: Inhibition by Triazoles", Corrosion Science, Jun. 1984, 10 pages.

Lewis, G., "Corrosion Inhibition of Copper by Benzimidazole", Corrosion SCI vol. 22, Iss. 6, (1982) pp. 579-584.

Zhang, D-Q. et al., "Synergistic effect of 2-mercapto benzimidazole and Kl on copper corrosion inhibition in aerated sulfuric acid solution", Journal of Applied Electrochemistry vol. 33, Iss. 5, (May 2003): pp. 361-366.

* cited by examiner

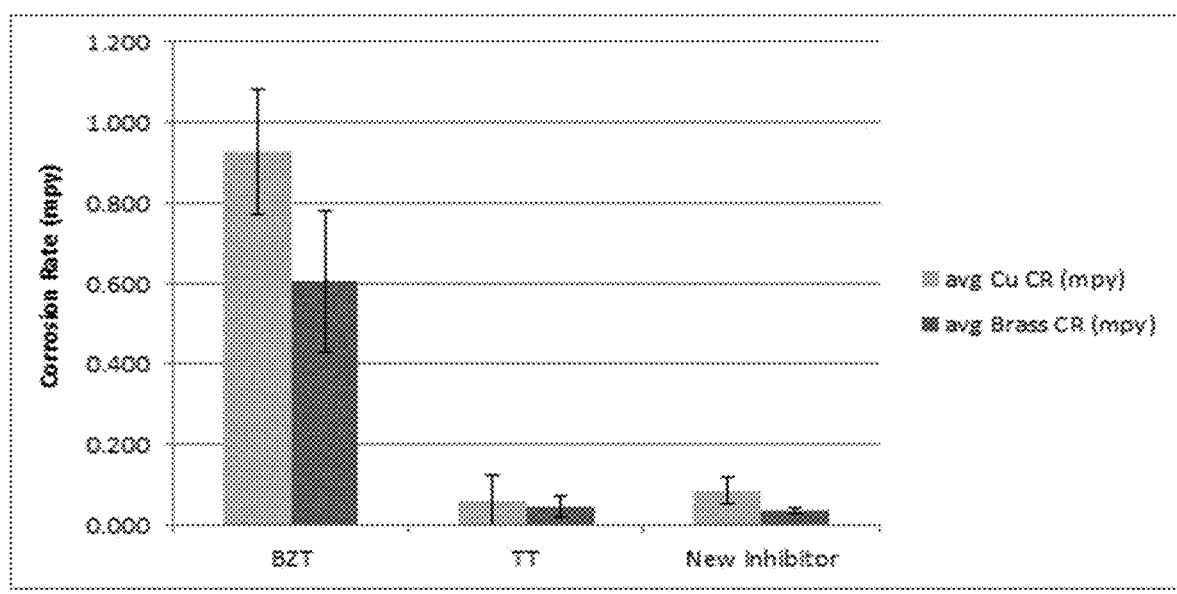

PROCESS AND METHOD FOR REDUCING METAL CORROSION IN WATER

BACKGROUND

1. Field of the Invention

The present disclosure generally relates to reducing corrosion of a metal surface in an aqueous system.

2. Description of the Related Art

Copper and copper alloy components are commonly used in industrial systems due to copper's high thermal conductivity and anti-microbial properties. Copper and copper alloys (e.g., bronze and brass) are relatively resistant to corrosion as a result of protective film layers that naturally coat the surface of copper, which include an inner cuprous oxide film layer and an outer cupric oxide film layer. Under anaerobic conditions, these protective layers generally reduce the rate of further corrosion of the metal surface. However, under certain conditions, copper and copper alloys are susceptible to corrosion, for example, in the presence of oxygen and under acidic conditions, oxidation of copper and dissolution of the copper (II) ion into water can occur.

Copper corrosion inhibitors are commonly added to industrial water systems to prevent and reduce dissolution of copper from system surfaces. For example, tolytriazole can inhibit the corrosion of copper and copper alloys. It is generally believed that the nitrogen lone pair electrons coordinate to the metal, resulting in the formation of a thin organic film layer that protects the copper surface from elements present in the aqueous system.

Oxidizing halogens are commonly used as biocides in industrial systems to control slime and microbiological growth in water. The protective film provided by many azoles erodes in the presence of oxidizing halogens such as chlorine, hypochlorite, and hypobromite, reducing the effectiveness of the corrosion inhibitor. Moreover, a decrease in copper (II) precipitation often occurs in the presence of oxidizing halogens due to halogen attack of the corrosion inhibitor in solution. Thus, in the presence of oxidizing halogens, an excess or continuous injection of corrosion inhibitor is often required to maintain the organic protective film.

BRIEF SUMMARY

In some embodiments, a method of reducing corrosion of a metal surface in an aqueous system is disclosed. The method can include adding a benzimidazole to an aqueous system comprising a metal surface; and adding a halogen selected from bromine, iodine, and any combination thereof to the aqueous system.

In some embodiments, the benzimidazole can be a compound of formula (I) or salt thereof,

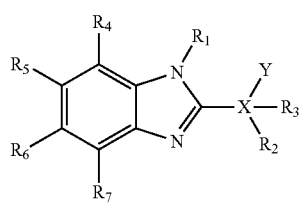

(I)

where $R^1$ can be halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl;

X can be absent, $CR^2R^3Y$, or $NR^2R^3Y$;

Y can be hydroxyl, halo, oxo, substituted or unsubstituted $C_1$-$C_{16}$ alkoxy, thiol, alkylthio, amino, hydrogen, or aminoalkyl;

$R^2$ and $R^3$ can be each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_8$ cycloalkyl, and substituted or unsubstituted $C_1$-$C_{16}$ alkyl; and $R^4$, $R^5$, $R^6$, and $R^7$ can be each independently selected from the group consisting of: hydrogen, halo, amino, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl, provided that at least one of $R^4$, $R^5$, $R^6$, and $R^7$ is hydrogen.

In some embodiments, the benzimidazole can be a compound of formula (II) or salt thereof,

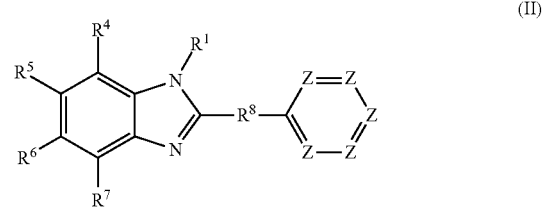

(II)

where $R^1$ can be hydrogen, a substituted or unsubstituted $C_1$-$C_{16}$ alkyl group, or a substituted or unsubstituted $C_4$-$C_6$ aryl group;

$R^8$ can be a bond or $CHR^9$;

$R^9$ can be hydrogen, halo, $NR^{10}R^{11}$, or $OR^{10}$;

wherein $R^{10}$ and $R^{11}$ can be each independently selected from the group consisting of: hydrogen, a substituted or unsubstituted $C_1$-$C_{12}$ alkyl group, and a substituted or unsubstituted $C_4$-$C_6$ aryl group; and Z can be independently nitrogen, $CR^4$, or $N^+R^{10}$.

In some embodiments, Z can be $CR^4$ and $R^4$ can be hydrogen.

In some embodiments, the halogen can be a bromine precursor, an iodine precursor, or any combination thereof.

In some embodiments, the method can include adding a halogen stabilizer that is an isocyanate, a hydantoin, sulfamic acid, ammonia, urea, an amine, or any combination thereof.

In some embodiments, the method can include measuring a corrosion rate of a metal surface in the aqueous system.

In some embodiments, the method can include adjusting a dosage of the compound of formula (I) or salt thereof to achieve a predetermined corrosion rate.

In some embodiments, the method can include adjusting a dosage of the halogen to achieve a predetermined corrosion rate.

In some embodiments, a dosage of the benzimidazole ranges from about 0.01 ppm to about 100 ppm.

In some embodiments, a dosage of the halogen ranges from about 0.01 ppm to about 100 ppm.

In some embodiments, the metal surface can be copper or a copper alloy.

In some embodiments, the aqueous system can include a biocide.

In some embodiments, the aqueous system can be chlorinated, brominated, iodated, or any combination thereof.

In other embodiments, a method of reducing corrosion of a metal surface in an aqueous system is disclosed that can include adding a compound of formula (I) or salt thereof to an aqueous system comprising a metal surface,

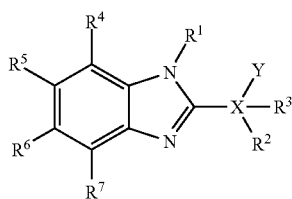

(I)

where $R^1$ can be halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl;

X can be absent, $CR^2R^3Y$, or $NR^2R^3Y$;

Y can be hydroxyl, halo, oxo, substituted or unsubstituted $C_1$-$C_{16}$ alkoxy, thiol, alkylthio, amino, hydrogen, or aminoalkyl;

$R^2$ and $R^3$ can be each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_6$ cycloalkyl, and substituted or unsubstituted $C_1$-$C_{16}$ alkyl; and $R^4$, $R^5$, $R^6$, and $R^7$ can be each independently selected from the group consisting of: hydrogen, halo, and substituted or unsubstituted $C_1$-$C_{16}$ alkyl, provided that at least one of $R^4$, $R^5$, $R^6$, or $R^7$ is fluoro, bromo, or iodo.

In some embodiments, a composition is disclosed. The composition can include a halogen selected from bromine, iodine, and any combination thereof; and a compound of formula (I) or salt thereof,

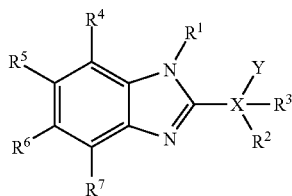

(I)

where $R^1$ can be halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl;

X can be absent, $CR^2R^3Y$, or $NR^2R^3Y$;

Y can be hydroxyl, halo, oxo, substituted or unsubstituted $C_1$-$C_{16}$ alkoxy, thiol, alkylthio, amino, hydrogen, or aminoalkyl;

$R^2$ and $R^3$ can be each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_6$ cycloalkyl, and substituted or unsubstituted $C_1$-$C_{16}$ alkyl; and $R^4$, $R^5$, $R^6$, and $R^7$ can be each independently selected from the group consisting of: hydrogen, halo, amino, aminoalkyl, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl, provided that at least one of $R^4$, $R^5$, $R^6$, and $R^7$ is hydrogen.

In some embodiments, X can be $CR^2R^3Y$; Y can be hydroxyl; and $R^2$ can be a substituted or unsubstituted $C_4$-$C_6$ aryl.

In certain embodiments, a use of the composition for reducing corrosion of a metal surface in an aqueous system is disclosed.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which:

FIG. 1 shows a comparison of corrosion rates of various inhibitors in the presence of chlorine residuals on brass and copper.

DETAILED DESCRIPTION

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

"Alkoxy" refers to a moiety of the formula RO—, where R is alkyl, alkenyl, or alkynyl.

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like.

"Alkylthio" refers to a moiety of the formula RS—, where R is alkyl, aryl, alkenyl, or alkynyl.

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Huckel's Rule.

"Carbonyl" refers to a substituent comprising a carbon double bonded to an oxygen. Examples of such substituents include aldehydes, ketones, carboxylic acids, esters, amides, and carbamates.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halo" refers to a fluoro group, chloro group, bromo group, or iodo group.

"Halogen Precursors" are species that are converted into biocidally effective halogen species upon introduction into the treated system.

"Heteroaryl" refers to a monocyclic or bicyclic 5-or 6-membered ring system, wherein the heteroaryl group is unsaturated and satisfies Huckel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Oxidizing Halogen" refers to a form of the halogen capable of performing oxidizing reactions in aqueous systems.

"Oxo" refers to an oxygen atom double-bonded to a carbon atom.

Total Residual Oxidant (TRO) refers to the concentration of oxidized halogen in solution. It is customarily shown as mg/l of $Cl_2$. In systems containing other oxidized halogens, the concentration is still presented as mg/l of $Cl_2$ even though, because of the molecular weight differences, the actual mg/l of the other halogen may differ. TRO represents the oxidizing capacity of the halogen residual, regardless of the mass concentration of the halogen.

Compounds of the present disclosure may be substituted with suitable substituents. The term "suitable substituent," as used herein, is intended to mean a chemically acceptable functional group, preferably a moiety that does not negate the activity of the compounds. Such suitable substituents include, but are not limited to, halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylaminocarbonyl groups, arylcarbonyl groups, aryloxy-carbonyl groups, alkylsulfonyl groups, and arylsulfonyl groups. In some embodiments, suitable substituents may include halogen, an unsubstituted $C_1$-$C_{12}$ alkyl group, an unsubstituted $C_4$-$C_6$ aryl group, or an unsubstituted alkoxy group. Those skilled in the art will appreciate that many substituents can be substituted by additional substituents.

The inventors have discovered an unexpectedly advantageous anticorrosion effect resulting from the combination of benzimidazole corrosion inhibitors with bromine or iodine-based biocides. It has been further discovered that this effect can be realized from "in situ" combination and formation of these components. It has even further been found that this effect can be realized "in-situ" by the combination of benzimidazole corrosion inhibitors and bromine or iodine-based biocides or biocide precursors in chlorinated water. The compounds of the present disclosure can be added directly to water along with bromine or Iodine-based biocides, such as BrCl or $Br_2$, eliminating the need for any additional pre-reaction of the benzimidazoles with the halogen species. Benzimidazoles can be reacted with bromine or iodine to produce halogen substitutions on the benzimidazole ring, and these compounds can be added to water without adding bromine or iodine-based biocides.

In some embodiments, a method of reducing corrosion of a metal surface in an aqueous system is disclosed. The method may include adding a benzimidazole to an aqueous system comprising a metal surface and adding a halogen selected from bromine, iodine, and any combination thereof to the aqueous system.

The compositions and methods of the present disclosure may include a benzimidazole that is a compound of formula (I) or salt thereof or a compound of formula (II) or salt thereof,

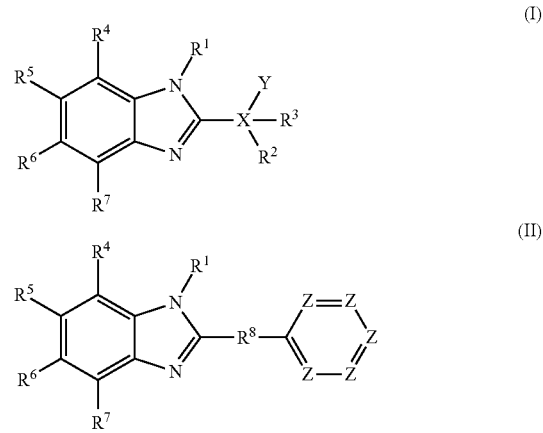

where $R^1$ is halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl.

In some embodiments, $R^1$ is hydrogen, a substituted or unsubstituted $C_1$-$C_{16}$ alkyl group, or a substituted or unsubstituted $C_4$-$C_6$ aryl group.

In some embodiments, $R^1$ is hydrogen.

In some embodiments, $R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_6$ cycloalkyl, and substituted or unsubstituted $C_1$-$C_{16}$ alkyl. In some embodiments, $R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, and substituted or unsubstituted $C_1$-$C_{16}$ alkyl. In some embodiments, $R^2$ and $R^3$ are each independently selected from the group consisting of: hydrogen and substituted or unsubstituted $C_4$-$C_6$ aryl. In some embodiments, $R^2$ is substituted or unsubstituted $C_4$-$C_6$ aryl, and $R^3$ is hydrogen.

In some embodiments, $R^4$, $R^5$, $R^6$, and $R^7$ are each independently selected from the group consisting of: hydrogen, halo, amino, aminoalkyl, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl. In some embodiments, at least one of $R^4$, $R^5$, $R^6$, and $R^7$ is hydrogen. In some embodiments, $R^4$, $R^5$, and $R^7$ are each hydrogen. In some embodiments, $R^4$ is hydrogen. In some embodiments, $R^5$ is hydrogen. In some embodiments, $R^6$ is hydrogen. In some embodiments, $R^7$ is hydrogen.

In some embodiments, $R^6$ is substituted or unsubstituted $C_1$-$C_{16}$ alkyl and $R^4$, $R^5$, and $R^7$ are each hydrogen. In some embodiments, $R^6$ is methyl and $R^4$, $R^5$, and $R^7$ are each hydrogen. In some embodiments, $R^6$ is halo and $R^4$, $R^5$, and $R^7$ are each hydrogen. In some embodiments, $R^6$ is chloro and $R^4$, $R^5$, and $R^7$ are each hydrogen. In some embodiments, $R^6$ is substituted or unsubstituted $C_1$-$C_{16}$ alkyl; $R^5$ is halo; and $R^4$ and $R^7$ are each hydrogen. In some embodiments, $R^6$ is methyl; $R^5$ is bromo; and $R^4$ and $R^7$ are each hydrogen. In some embodiments, $R^4$, $R^5$, $R^6$, and $R^7$ are each hydrogen. Preferably, $R^4$, $R^5$, $R^6$, and $R^7$ are each hydrogen or at least one of $R^4$, $R^5$, $R^6$, and $R^7$ is substituted or unsubstituted $C_1$-$C_{16}$ alkyl and the remaining substituents are hydrogen.

In some embodiments, $R^8$ is a bond or $CHR^9$. In some embodiments, $R^8$ is a bond. In some embodiments, $R^8$ is $CHR^9$. $R^9$ can be hydrogen, halo, $NR^{10}R^{11}$, or $OR^{10}$. In some embodiments, $R^{10}$ and $R^{11}$ are each independently selected from the group consisting of: hydrogen, a substituted or unsubstituted $C_1$-$C_{12}$ alkyl group, and a substituted or unsubstituted $C_4$-$C_6$ aryl group. In some embodiments, $R^8$ is $CHR^9$, $R^9$ is $OR^{10}$, and $R^{10}$ is hydrogen.

In some embodiments, X is absent, $CR^2R^3Y$, or $NR^2R^3Y$. In some embodiments, X is absent. In some embodiments, X is $CR^2R^3Y$. In some embodiments, X is $NR^2R^3Y$.

In some embodiments, X is absent and $R^4$, $R^5$, $R^6$, and $R^7$ are each hydrogen. In some embodiments, X is $CR^2R^3Y$; Y is hydroxyl; and $R^2$ is a substituted or unsubstituted $C_4$-$C_6$ aryl.

In some embodiments, Y is hydroxyl, halo, oxo, substituted or unsubstituted $C_1$-$C_{16}$ alkoxy, thiol, alkylthio, amino, hydrogen, or aminoalkyl. In some embodiments, Y is hydroxyl.

In some embodiments, Z is independently nitrogen, $CR^4$, or $N^+R^{10}$. In some embodiments, Z is $CR^4$. In some embodiments, one Z is nitrogen and the rest are $CR^4$. In some embodiments, at least two Z atoms are nitrogen and the rest are $CR^4$. In some embodiments, Z is $CR^4$ and $R^4$ is hydrogen. In some embodiments, $R^8$ is a bond and at least one Z is nitrogen.

In some embodiments, the compound or salt thereof of formula (I) or formula (II) is

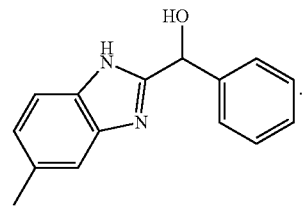 [SMILES: Cc1ccc2[nH]c(C(O)c3ccccc3)nc2c1]

In some embodiments, the compound or salt thereof of formula (I) or formula (II) is

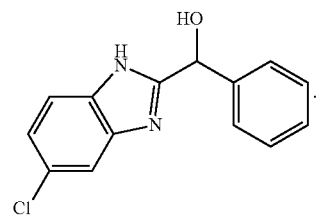 [SMILES: OC(c1ccccc1)c1nc2cc(Cl)ccc2[nH]1]

In some embodiments, the compound or salt thereof of formula (I) or formula (II) is

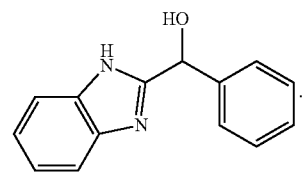 [SMILES: OC(c1ccccc1)c1nc2ccccc2[nH]1]

In some embodiments, the compound or salt thereof of formula (I) or formula (II) is

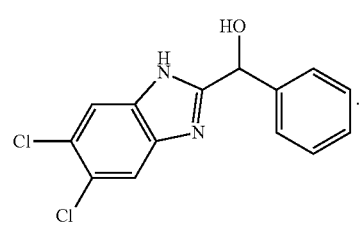 [SMILES: OC(c1ccccc1)c1nc2cc(Cl)c(Cl)cc2[nH]1]

In some embodiments, the compound or salt thereof of formula (I) or formula (II) is

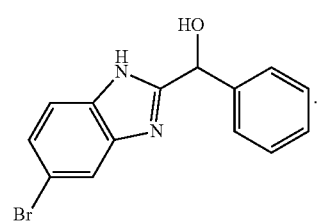

In some embodiments, the compound or salt thereof of formula (I) or formula (II) is

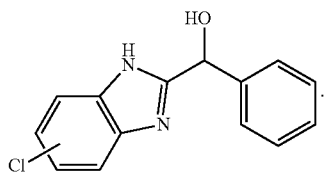

In some embodiments, the compound or salt thereof of formula (I) or formula (II) is

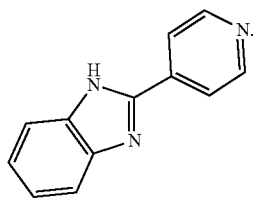 [SMILES: c1ccc2[nH]c(-c3ccncc3)nc2c1]

In some embodiments, the compound or salt thereof of formula (I) or formula (II) is

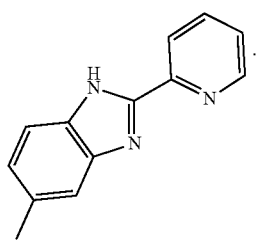 [SMILES: Cc1ccc2[nH]c(-c3ccccn3)nc2c1]

In some embodiments, the compound or salt thereof of formula (I) or formula (II) is

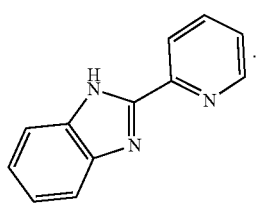 [SMILES: c1ccc(-c2nc3ccccc3[nH]2)nc1]

In some embodiments, the compound or salt thereof of formula (I) or formula (II) is

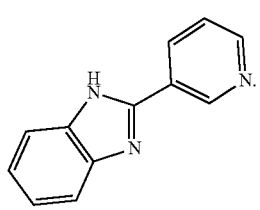 [SMILES: c1cncc(-c2nc3ccccc3[nH]2)c1]

In some embodiments, the compound or salt thereof of formula (I) or formula (II) is

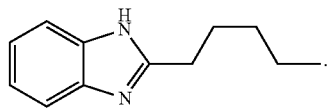

In some embodiments, the compound or salt thereof of formula (I) or formula (II) is

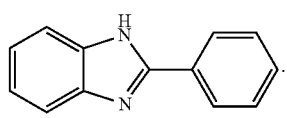 [SMILES: c1ccc(-c2nc3ccccc3[nH]2)cc1]

In some embodiments, the compound or salt thereof of formula (I) is

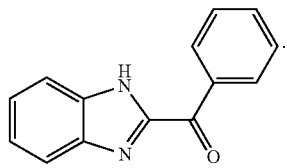 [SMILES: O=C(c1ccccc1)c1nc2ccccc2[nH]1]

In some embodiments, the compound or salt thereof of formula (I) is

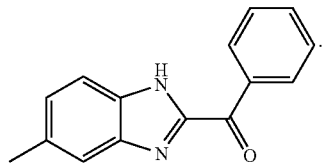 [SMILES: Cc1ccc2[nH]c(C(=O)c3ccccc3)nc2c1]

In certain embodiments, the salt of the compound of formula (I) may be any salt, such as a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In some embodiments, salt of the compound of formula (I) may be a hydrochloride or sulfate salt. The salt form of the compounds can include N-protonated benzimidazole with any suitable counter ion.

The compositions of the present disclosure may include a halogen selected from bromine, iodine, and any combination thereof. In addition, the compositions of the present disclosure may include a halogen stabilizer.

In some embodiments, the halogen is bromine, iodine, or any combination thereof. In some embodiments, the halogen is bromine. In some embodiments, the halogen may include any bromine- or iodine-containing biocide. Bromine may be in the form of bromide salts, such as sodium bromide. Other forms of bromine include but are not limited to hypobromite salts, such as sodium hypobromite.

Halogens can exist in several oxidation states, but only some of them are effective as biocontrol agents. In the elemental (zero valent) form they are found in nature as the $X_2$ molecule where X represents any halogen. When dissolved in water the halogens undergo a disproportionation reaction:

$$X_2 + H_2O \rightarrow HOX + HX \qquad \text{Reaction 1:}$$

which leaves half of the halogen in the −1 oxidation state and half in the +1 oxidation state. It is well established in the art that the HOX or its conjugate base $OX^-$ are the biocidally effective form of the halogens and halide ions in the $X^-$ form do not contribute to microbiological control.

In their elemental form, the halogens are hazardous to store and handle, because of their physical form (toxic corrosive gas or liquid). For large applications chlorine gas is sometimes used directly, and for some specialty applications bromine chloride gas or solid Iodine may be applied. $Br_2$ liquid is not commonly used for biocidal control.

It is increasingly common to use chlorine as a pre-prepared salt, such as sodium hypochlorite (commonly known as bleach), as the delivered form of chlorine biocides. Sodium hypobromite or hypoiodite are generally not stable enough in concentrated form to be a viable form for delivery.

Bromine-based biocides have some well-known biocidal advantages. Because of a lack of stability, bromine-based biocides are generally delivered as precursors, which convert in-situ into biocidally effective forms, such as oxidized bromine.

A common method of producing biocidal bromine is the reaction of a bromide salt with a chlorine residual in the system, as described by the following reaction:

$$HOCl + Br^- \rightarrow HOBr + Cl^- \qquad \text{Reaction 2:}$$

Reaction 2 occurs quickly and completely in dilute (ppm) concentrations.

Another means of delivering oxidized bromine is through the use bromine-containing precursors containing the functional group: R—N—Br where the R—N functionality can be ammonia, sulfamic acid, isocyanuric acid, urea, or hydantoins. In these molecules, bromine exists in the +2 oxidation state and can undergo the equilibrium reaction:

$$R-N-Br + H_2O \rightarrow RNH_2 + HOBr \qquad \text{Reaction 3:}$$

These nitrogen-containing compounds are also added to treated systems in the unhalogenated form to reduce the reactivity and extend the effective life of the halogen in the system. In this role, they are defined as "Stabilizers."

In some embodiments, a halogen stabilizer may be added to the system. A stabilizer can be added to provide the stability for oxidizing biocide in the application environment. For example, halogen stabilizers include ammonia, urea, sulfamic acid, hydantoin compounds and isocyanuric acid compounds.

In some embodiments, the halogen can be in the oxidizing form prior to adding to the aqueous system. In some embodiments, halogen can be in a precursor form prior to addition to the aqueous system, and formed in-situ through reaction with chlorine. For example, a bromine precursor can be bromide ion ($Br^-$) and an iodine precursor can be iodide ion ($I^-$).

In some embodiments, a method of reducing corrosion of a metal surface in an aqueous system is disclosed. The method includes adding a compound of formula (I), formula (II), or salts thereof and a halogen to an aqueous system.

While the compounds of formulae (I) or (II) can be added to an aqueous system at any dosage rate, the compounds of formulae (I) and (II) are generally added to an aqueous system at a dosage rate of from about 0.01 ppm to about 500 ppm. In certain embodiments, a compound of formula (I) or (II) is added to an aqueous system at a dosage rate of from about 0.01 ppm to about 100 ppm. In certain embodiments, a compound of formula (I), (Ia), or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

While the halogen can be added to an aqueous system at any dosage rate, the halogen is generally added to an aqueous system at a dosage rate of from about 0.01 ppm to about 500 ppm. In certain embodiments, a halogen is added to an aqueous system at a dosage rate of from about 0.01 ppm to about 100 ppm. In certain embodiments, halogen is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

One of skill in the art will appreciate that the dosage of benzimidazole or the dosage of halogen may be outside the disclosed ranges depending on the conditions of the aqueous system and the desired corrosion rate.

In some embodiments, the methods disclosed herein may include measuring a corrosion rate of a metal surface in the aqueous system. Methods of measuring corrosion rates of metal surfaces are well known in the art, and one of ordinary skill in the art would be able to select the appropriate method.

In some embodiments, the methods disclosed herein may include adjusting a dosage of the compound of formula (I), formula (II), or salts thereof to achieve a predetermined corrosion rate.

In some embodiments, the methods disclosed herein may include adjusting a dosage of the halogen to achieve a predetermined corrosion rate.

The predetermined corrosion rate may be about 0.2 mpy or less. In certain embodiments, the predetermined corrosion rate is about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

In some embodiments, the aqueous system is an industrial water system. "Industrial water system" means any system that circulates water as its primary ingredient. Non-limiting examples of "industrial water systems" include cooling systems, boiler systems, heating systems, membrane systems, papermaking systems, or any other systems that circulate water.

In certain embodiments, the aqueous system is a cooling water system. The cooling water system can be a closed loop cooling water system or an open loop cooling water system.

In some embodiments, the aqueous system may include a biocide. In some embodiments, the aqueous system can be chlorinated, brominated, or iodated. In some embodiments, the aqueous system can be chlorinated. An advantage of the disclosed compositions and methods is that compounds of formulae (I) and (II) generally provide corrosion protection for metal surfaces in the presence of oxidizing halogens. In certain embodiments, a compound of formula (I) or (II) is added to an aqueous system in contact with a metal surface and provides corrosion protection for metal surface in the presence of any oxidizing halogen compound. In certain embodiments, a compound of formula (I) or (II) inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof. While not wishing to be bound by any particular theory, it is postulated that the relatively large number of heteroatoms of the compounds of formulae (I) and (II) provide a greater number of sites for bonding to metal surfaces and metal ions, which can provide enhanced corrosion inhibition as compared to many existing corrosion inhibitors. In addition, it is postulated that the compounds of formulae (I) and (II) form stable films because the compounds can form a 1,2-chelation complex with metal.

When the compounds of the present disclosure are combined with bromine compounds in an aqueous system, an unexpected decrease in the corrosion rate is observed. It is well established that oxidizing halogens increase the corrosion of copper and copper alloys. Therefore, it was surprising to find a decrease in the corrosion rate when oxidizing halogen or oxidizing halogen precursor was added with the benzimidazoles of the present disclosure. Without being bound by any particular theory, it is believed that the oxidizing halogen in solution reacts with the benzimidazole ring to produce halogenated benzimidazoles that exhibit surprising anti-corrosion properties.

In certain embodiments, a compound of formula (I) or (II) inhibits metal corrosion when added to an aqueous system comprising a non-halogen-containing oxidizing biocide including, but not limited to, peroxides (e.g., hydrogen peroxide), ozone, persulfates, permanganates, and peracetic acids.

The methods and the compositions of the present disclosure may provide corrosion protection for any metal or metal alloy including, but not limited to, copper, iron, silver, steel (e.g., galvanized steel), zinc alloy, and aluminum. In certain embodiments, the compositions disclosed herein may be added to an aqueous system in contact with a metal surface comprising copper to inhibit metal corrosion. In certain embodiments, the compositions disclosed herein may be added to an aqueous system in contact with a metal surface comprising a copper alloy to inhibit metal corrosion. In certain embodiments, copper complexes with one or more heteroatoms in a compound of formula (I) or (II). In certain embodiments, copper complexes with one or more heteroatoms in a compound of formula (I) or (II). Copper has a wide-range of applications, including use as copper piping and tubing in plumbing and industrial machinery. Copper and copper alloys are well known for their use in cooling water and boiler water systems. In some embodiments, the metal surface may include copper.

The compositions and methods disclosed herein can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, any of the compositions disclosed herein is added to an aqueous system in contact with a metal surface comprising bronze to inhibit metal corrosion. In certain embodiments, any of the compositions disclosed herein is added to an aqueous system in contact with a metal surface comprising brass, for example admiralty brass, to inhibit metal corrosion. In certain embodiments, any of the compositions disclosed herein is added to an aqueous system in contact with a metal surface comprising a copper-nickel alloy to inhibit metal corrosion.

In certain embodiments, the methods and compositions disclosed herein inhibit the corrosion of mild steel. In certain embodiments, the methods and compositions disclosed herein inhibit the corrosion of metal alloys including, but not limited to, galvanized steel, stainless steel, cast iron, nickel, and combinations thereof. While not wishing to be bound by any particular theory, it is postulated that the compounds of formulae (I) and (II) inactivate Cu (II) in solution, preventing the occurrence of galvanic cells on the steel surface. While not wishing to be bound by any particular theory, it is also postulated that the compounds of formula (I) or (II) react with bromine or iodine in solution to produce halo-substituted benzimidazole rings that exhibit unexpected corrosion inhibition properties.

In other embodiments, the inclusion of a halogen in the composition or adding a halogen to an aqueous system may be optional. In embodiments where a halogen is optional, the compound of formula (I) or salt thereof may have a bromo or iodo group in at least one of $R^4$, $R^5$, $R^6$, and $R^7$ positions.

In certain embodiments, a method of reducing corrosion of a metal surface in an aqueous system is disclosed. The method may include adding a compound of formula (I) or salt thereof to an aqueous system comprising a metal surface.

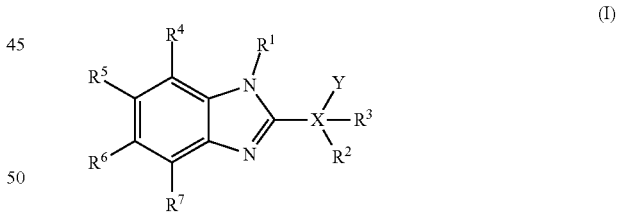

(I)

where $R^1$ is halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl;

X is absent, $CR^2R^3Y$, or $NR^2R^3Y$;

Y is hydroxyl, halo, oxo, substituted or unsubstituted $C_1$-$C_{16}$ alkoxy, thiol, alkylthio, amino, hydrogen, or aminoalkyl;

$R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_6$ cycloalkyl, and substituted or unsubstituted $C_1$-$C_{16}$ alkyl; and $R^4$, $R^5$, $R^6$, and $R^7$ are each independently selected from the group consisting of: hydrogen, halo, and substituted or unsubstituted $C_1$-$C_{16}$ alkyl, provided that at least one of $R^4$, $R^5$, $R^6$, or $R^7$ is fluoro, bromo, or iodo.

In some embodiments, the method may include adding a compound of formula (II) or formula (III) or salt thereof.

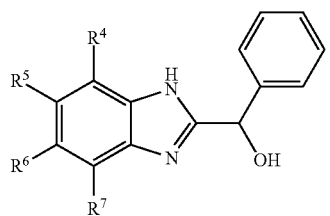

(III)

For formulae (I)-(III), $R^6$ may be bromo. In some embodiments, $R^5$ and $R^6$ may be bromo or iodo. In some embodiments, $R^5$ and $R^6$ may be bromo. In some embodiments, $R^4$, $R^5$, and $R^6$ may be bromo or iodo. In some embodiments, $R^5$, $R^6$, and $R^7$ may be bromo or iodo. In some embodiments, $R^4$, $R^5$, $R^6$, and $R^7$ may be bromo or iodo.

In some embodiments, the compound of formulae (I)-(III) or salt thereof is selected from the group consisting of:

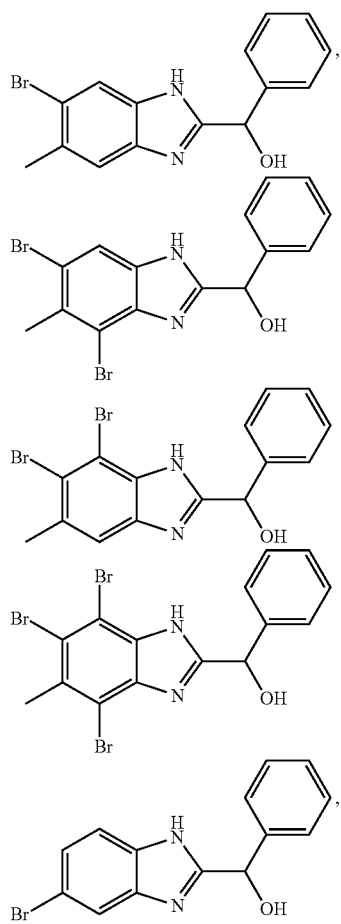

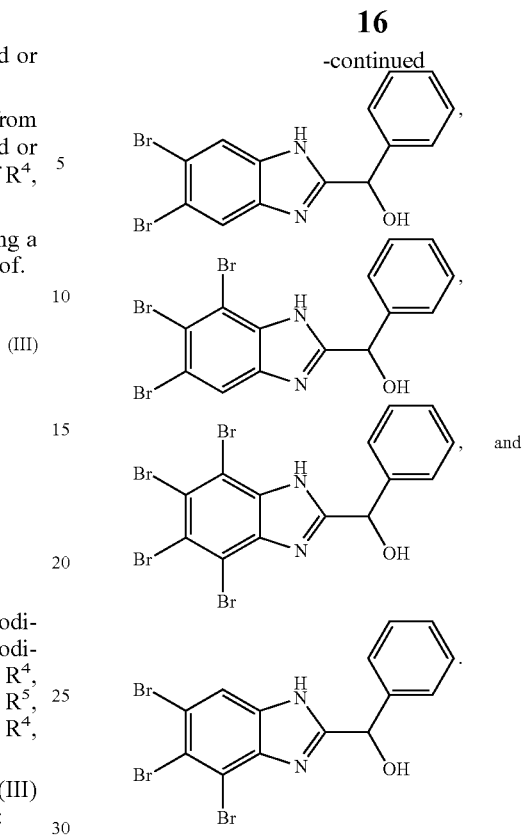

In some embodiments, the compound of formula (I) or salt thereof is

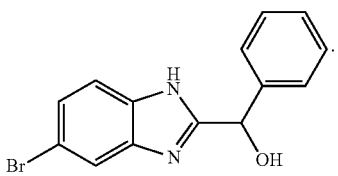 [SMILES: OC(c1ccccc1)c1nc2cc(Br)ccc2[nH]1]

In some embodiments, the compound of formula (I) or salt thereof is

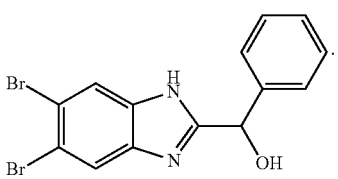 [SMILES: OC(c1ccccc1)c1nc2cc(Br)c(Br)cc2[nH]1]

In some embodiments, the concentration of the compound or salt thereof of formula (I) or formula (II) in the composition may range from about 1 wt % to about 50 wt %, about 5 wt % to about 50 wt %, about 10 wt % to about 50 wt %, about 15 wt % to about 50 wt %, about 20 wt % to about 50 wt %, about 20 wt % to about 45 wt %, about 25 wt % to about 45 wt %, or about 25 wt % to about 40 wt %. In some embodiments, the composition may include water.

In some embodiments, the compounds of formulae (I) and (II) are contacted with a metal surface by any suitable method. In certain embodiments, a solution comprising a compound of formula (I) or (II) is contacted with a metal surface by immersion, spraying, or other coating techniques. In certain embodiments, a solution comprising a halogen and a compound of formula (I) or (II) is contacted with a metal surface by immersion, spraying, or other coating techniques. In certain embodiments, a solution comprising a compound of formula (I) or (II) is introduced into the water of the aqueous system by any conventional method and is fed into the aqueous system on either a periodic or continuous basis.

In some embodiments, the compositions disclosed herein may include a fluorescent organic compound. In certain embodiments, the fluorescent organic compound may be selected from Rhodamine or derivatives thereof, an acridine dye, fluorescein or derivatives thereof, and combinations thereof. In certain embodiments, the compositions disclosed herein may include a fluorescent tagged polymer.

Those skilled in the art will appreciate that a compound of formula (I) or (II) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I) or formula (II). Moreover, a compound of formula (I) or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I) and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

The methods and compositions disclosed herein can be used to inhibit corrosion of metal in an aqueous system having any pH. In certain preferred embodiments, a compound of formula (I) or (II) is added to an aqueous system having a pH of from about 6 to about 12. Thus, in certain preferred embodiments, a compound of formula (I) or (II) is added to an aqueous system having a pH of from about 6 to about 12, from about 6 to about 11, from about 6 to about 10, from about 6 to about 9, from about 6 to about 8, from about 7 to about 12, from about 8 to about 12, from about 9 to about 12, from about 7 to about 10, or from about 8 to about 10.

TABLE 1

| | |
|---|---|
| 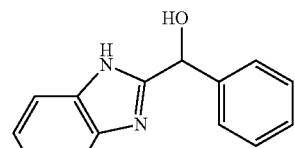 | Compound 1 |
| 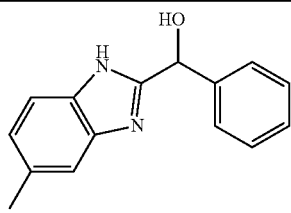 | Compound 2 |

TABLE 1-continued

| | |
|---|---|
| 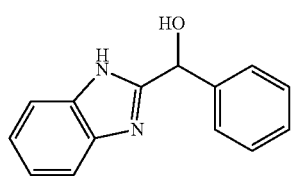 [SMILES: OC(c1ccccc1)c1nc2ccccc2[nH]1] | Compound 3 |
| 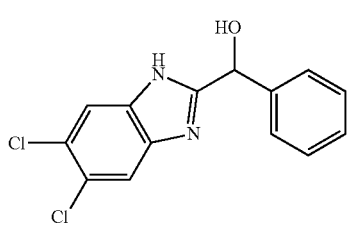 | Compound 4 |
| 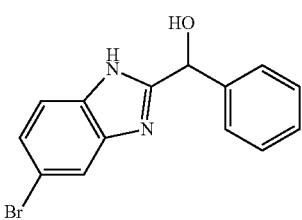 [SMILES: OC(c1ccccc1)c1nc2cc(Cl)ccc2[nH]1] | Compound 5 |
| 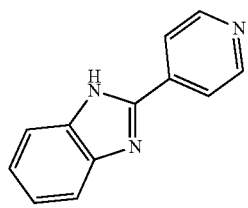 [SMILES: c1ccc2[nH]c(-c3ccncc3)nc2c1] | Compound 6 |
| 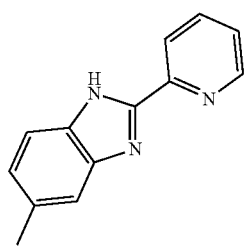 [SMILES: Cc1ccc2[nH]c(-c3ccccn3)nc2c1] | Compound 7 |
| 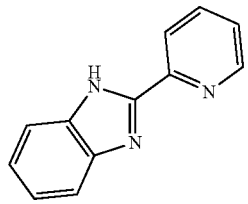 [SMILES: c1ccc(-c2nc3ccccc3[nH]2)nc1] | Compound 8 |
| 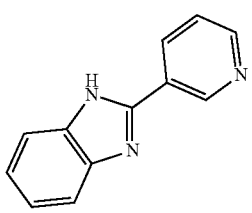 [SMILES: c1cncc(-c2nc3ccccc3[nH]2)c1] | Compound 9 |

TABLE 1-continued

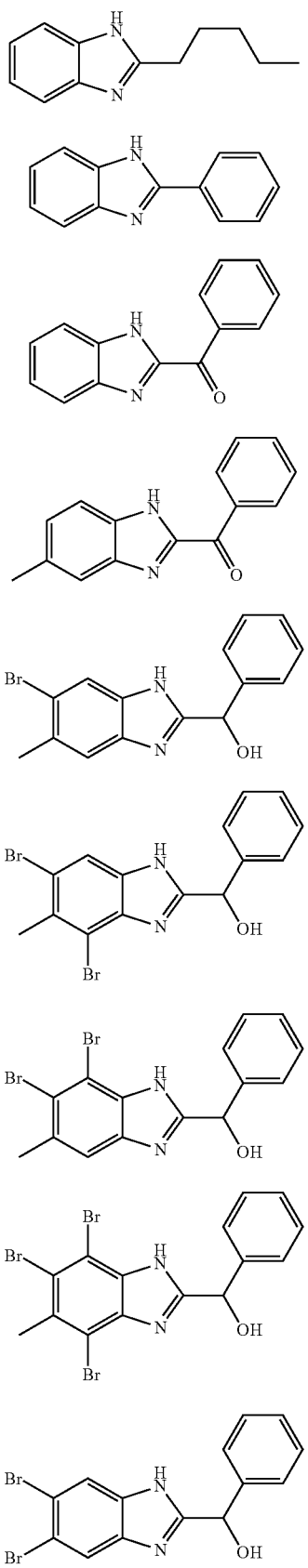

Compound 10

Compound 11

Compound 12

Compound 13

Compound 14

Compound 15

Compound 16

Compound 17

Compound 18

TABLE 1-continued

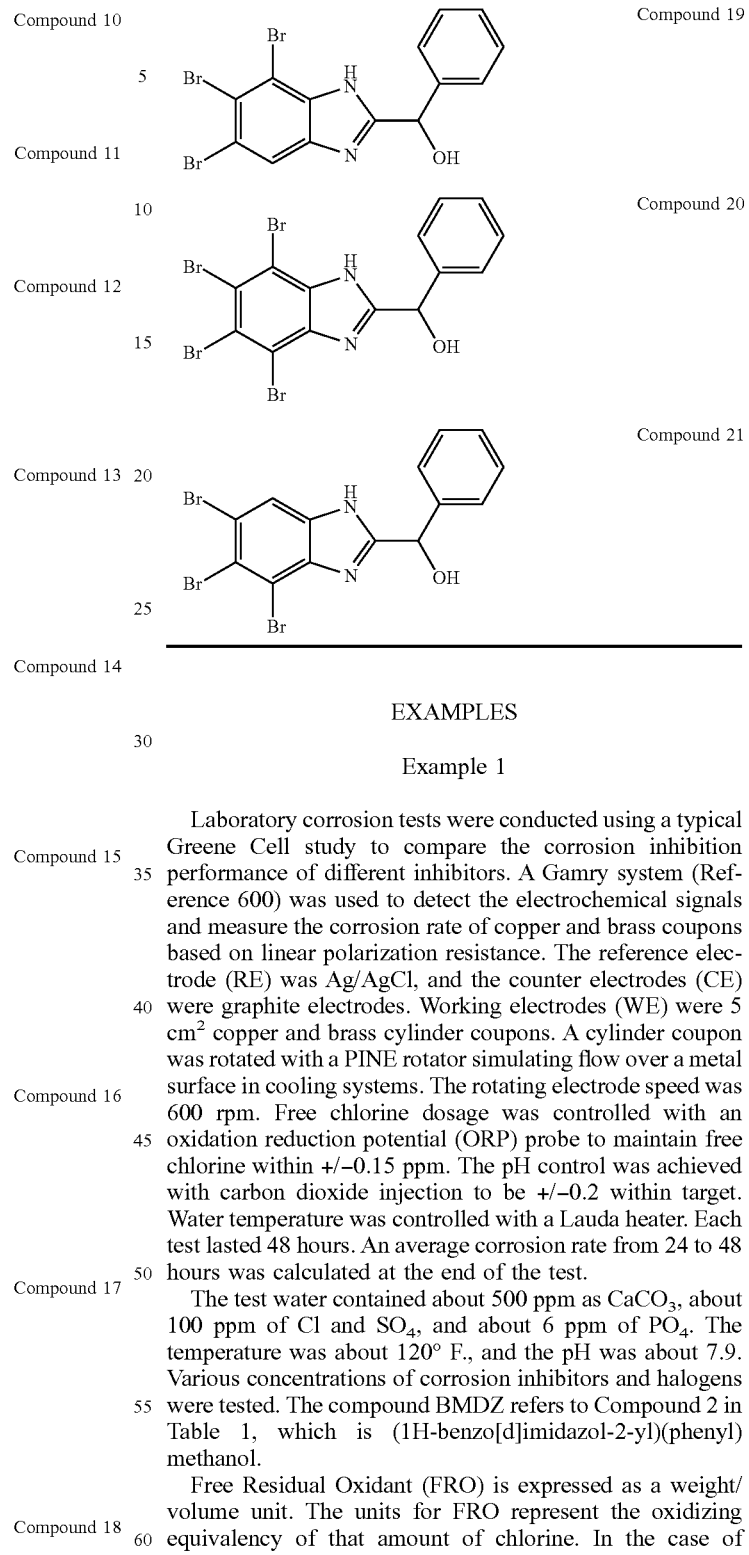

Compound 19

Compound 20

Compound 21

EXAMPLES

Example 1

Laboratory corrosion tests were conducted using a typical Greene Cell study to compare the corrosion inhibition performance of different inhibitors. A Gamry system (Reference 600) was used to detect the electrochemical signals and measure the corrosion rate of copper and brass coupons based on linear polarization resistance. The reference electrode (RE) was Ag/AgCl, and the counter electrodes (CE) were graphite electrodes. Working electrodes (WE) were 5 cm² copper and brass cylinder coupons. A cylinder coupon was rotated with a PINE rotator simulating flow over a metal surface in cooling systems. The rotating electrode speed was 600 rpm. Free chlorine dosage was controlled with an oxidation reduction potential (ORP) probe to maintain free chlorine within +/−0.15 ppm. The pH control was achieved with carbon dioxide injection to be +/−0.2 within target. Water temperature was controlled with a Lauda heater. Each test lasted 48 hours. An average corrosion rate from 24 to 48 hours was calculated at the end of the test.

The test water contained about 500 ppm as $CaCO_3$, about 100 ppm of Cl and $SO_4$, and about 6 ppm of $PO_4$. The temperature was about 120° F., and the pH was about 7.9. Various concentrations of corrosion inhibitors and halogens were tested. The compound BMDZ refers to Compound 2 in Table 1, which is (1H-benzo[d]imidazol-2-yl)(phenyl)methanol.

Free Residual Oxidant (FRO) is expressed as a weight/volume unit. The units for FRO represent the oxidizing equivalency of that amount of chlorine. In the case of bromine or iodine, the actual weight of substance producing a given FRO will be higher than the weight of chlorine to give that FRO. When bromine is added to the water, any bromide ions react completely with the chlorine to form HOBr/OBr—.

Pickering (U.S. Pat. No. 5,411,677) describes a composition and method for preventing copper corrosion in acidic media by combining a benzotriazole and halide ions. The corrosion processes in this environment differ significantly from the process of the present application in that, in the present application, the solutions are at neutral to slightly alkaline pH, and contain a residual of oxidized halogen. Table 2 shows corrosion rates of copper and brass in water that is treated with BMDZ and halide ions. This example, using the procedure described previously shows little advantage under relevant conditions to the combination of BMDZ with halide ions. Oxidized chlorine reduces the performance of azole copper corrosion inhibitors. The data in Table 2 illustrates that the performance of the benzimidazoles of the present application, while more resistant to this effect than other corrosion inhibitors, the benzimidazoles are still negatively impacted by the presence of an oxidizing chlorine residual.

TABLE 2

Corrosion rates seen with inhibitors and bromide (and Iodide) ions with no oxidant

| Scenario | Corrosion Rate (mpy) | Presence of oxidant | Presence of halide Ion |
|---|---|---|---|
| 2.5 ppm BMDZ/Cu | 0.0015 | no oxidant | Yes. chloride |
| 2.5 ppm BMDZ/Brass | 0.0022 | no oxidant | Yes. chloride |
| 2.5 ppm BMDZ/Cu | 0.001 | no oxidant | Yes. bromide |
| 0 ppm BMDZ/Cu | 0.002 | no oxidant | Yes. bromide |
| 0 ppm BMDZ/Cu | 0.0016 | no oxidant | Yes. chloride |
| 0 ppm BMDZ/Brass | 0.0022 | no oxidant | Yes. chloride |

FIG. 1 shows a comparison of corrosion rates of various inhibitors in the presence of chlorine residuals on brass and copper. BZT is benzotriazole, TT is tolyltriazole, and new inhibitor is BMDZ. In the presence of about 0.5 ppm free chlorine, pH about 7.9. Inhibitor about 2 ppm.

Table 3 shows corrosion rates of copper and brass in water that is in the presence of oxidant and halide ions. When oxidizing chlorine is present in the water a significant increase in corrosion rates.

TABLE 3

Corrosion rates in presence of oxidant (oxidized halogen)

| Scenario | Corrosion Rate (mpy) | Presence of oxidant | Presence of halide Ion |
|---|---|---|---|
| No Inhibitor/Cu | 0.55 | 0.5 ppm free chlorine | Yes. chloride |
| No Inhibitor/Brass | 0.88 | 0.5 ppm free chlorine | Yes. chloride |
| No Inhibitor/Cu | 0.0016 | 0 ppm free chlorine | Yes. chloride |
| No Inhibitor/Brass | 0.0022 | 0 ppm free chlorine | Yes. chloride |

Example 2

Hoover and Bush (U.S. Pat. No. 4,818,413) describe a process whereby copper corrosion is reduced through the combination of bromide ion and oxidized chlorine in industrial process water. When bromide ion and oxidized chlorine are combined without a benzimidazole corrosion inhibitor in industrial process water, little to no corrosion protection is provided. Table 4 shows that little advantage is obtained in the absence of an organic heterocycle inhibitor. Corrosion rates were measured for water treated with chlorine and bromide ions in the absence of an inhibitor.

TABLE 4

Copper/brass corrosion rates resulting from addition of chlorine and bromine biocides without corrosion inhibitor

| Corrosion Inhibitor/ Metal | Average Corrosion Rate in presence of 0.6 ppm free halogenated biocide (mpy) | Halogenated Biocide |
|---|---|---|
| None/Brass | 0.1672 | Bromide ions in chlorinated water |
| None/Brass | 0.2411 | Chlorinated water |
| None/Cu | 1.2531 | Bromide ions in chlorinated water |
| None/Cu | 0.9729 | Chlorinated water |

Example 3

This example illustrates an unexpected advantage of the disclosed methods and compounds. Table 5 shows the dramatic reduction of the corrosion rates of brass when all the elements of the invention are present. With the corrosion inhibitor, BMDZ, in bromine-based biocide, the corrosion rate (CR) decreased over 99%, while BMDZ achieved a corrosion rate decrease of 91% in chlorinated water in the absence of bromide ions. The corrosion rate with BMDZ in presence of bromine-based biocide was one order of magnitude lower than that in presence of free chlorine. This shows that BMDZ was unexpectedly effective in the presence of bromine.

TABLE 5

Brass corrosion inhibition performance resulting from addition of chlorine and bromine biocides

| Corrosion Inhibitor | Average Corrosion Rate in presence of 0.6 ppm free halogenated biocide (mpy) | Halogenated Biocide |
|---|---|---|
| None | 0.1672 | Bromide ions in chlorinated water |
| BMDZ 2.5 ppm/Brass | 0.0011 | Bromide ions in chlorinated water |
| BMDZ 2.5 ppm | 0.004 | Iodide ions in chlorinated water |
| None | 0.2411 | Chlorinated water |
| BMDZ 2.5 ppm | 0.0355 | Chlorinated water |

Table 6 shows the dramatic reduction of the corrosion rates of copper. The same dramatic reduction in corrosion rate was observed for copper.

TABLE 6

Copper corrosion inhibition performance resulting from addition of chlorine and bromine biocides

| Corrosion Inhibitor/ Metal | Average Corrosion Rate in presence of 0.6 ppm free halogenated biocide (mpy) | Halogenated Biocide |
|---|---|---|
| None/Cu | 1.2531 | Bromide ions in chlorinated water |
| BMDZ 2.5 ppm/Cu | 0.0045 | Bromide ions in chlorinated water |
| None/Cu | 0.9729 | Chlorinated water |
| BMDZ 2.5 ppm/Cu | 0.0847 | Chlorinated water |

Example 4

This example shows the beneficial effect when the inhibitors are used in conjunction with a stabilized bromine as the source of oxidized halogen. The stabilizer used in this example was sulfamic acid.

TABLE 7

Copper corrosion inhibition performance resulting from addition of chlorine and bromine biocides

| Corrosion Inhibitor (5 ppm) | Average Corrosion Rate with no bleach (mpy) | Average Corrosion Rate in presence of 1 ppm free halogen (mpy) | Halogenated Biocide | %Change in Corrosion Rate due to Biocide Addition |
|---|---|---|---|---|
| Me-BMDZ | 0.0021 | 0.0127 | Bleach | +505 |
| BMDZ | 0.0048 | 0.0335 | Bleach | +598 |
| Me-BMDZ | 0.0014 | 0.001 | Stabilized bromine | −29 |
| BMDZ | 0.0042 | 0.0018 | Stabilized bromine | −57 |
| Me-BMDZ | 0.0029 | 0.0022 | Stabilized bromine and Bleach* | −24 |
| BMDZ | 0.0028 | 0.0072 | Stabilized bromine and Bleach* | +157 |

*The molar ratio of chlorine to bromide in solution was 4:1.

Example 5

The reaction products formed in situ during a given corrosion experiment were determined by high-performance liquid chromatography (HPLC). Identification of the HPLC peaks of specific analogs was done by a combination of HPLC with ultraviolet photodiode array spectroscopy and high-resolution mass spectrometry detection (HPLC-UV-MS), HPLC with retention time matching of known standards, and nuclear magnetic resonance spectroscopy (NMR).

An HPLC-UV profile was obtained for in situ chlorine and bromine experiments and observed formation of new peaks upon loss of the parent compound (BMDZ). By UV and MS detection, the new peaks were determined to be ketone derivatives in the presence of chlorine and brominated derivatives in the presence of bromine. The high-resolution MS spectra found that BMDZ was mono-, di-, tri-, and tetra-substituted when exposed to bromine in solution. Standards for keto and mono-halogenated reaction products were synthesized and their HPLC retention times compared to in situ product peaks.

A combined NMR and HPLC study was used to assign the identities of the halogenated analogs to the HPLC profiles. Halogenation experiments for Me-BMDZ and BMDZ were performed in an NMR sample tube at concentrations amenable to product identification. From the proton NMR analysis, the position of the halogenation was identified, and the relative concentration ratios of the major halogenation products determined. The NMR concentration ratios were compared to the UV and MS ratios from HPLC peaks of the same reaction samples to assign a chemical structure to the major HPLC peaks. Halogenation has only been observed on the benzimidazole aromatic ring. Without being bound by any particular theory, halogenation only occurred on the benzimidazole ring because of fast exchange of the imidazole proton, the 4 and 7 positions as well as the 5 and 6 positions of the benzimidazole positions are spectroscopically equivalent. NMR data indicates that halogenation is favored at the 5 and 6 positions over the 4 and 7 positions. The favored mono-halogenated product would be substituted in the 5 position and the favored dihalogenated product would be substituted in the 5 and 6 positions.

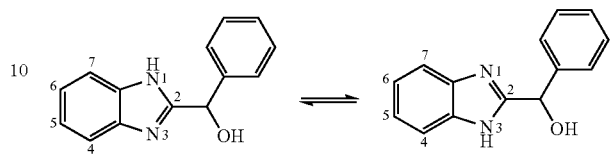

Depending on the exposure of the Me-BMDZ and BMDZ to the halogenation conditions, multiple mono, di, tri and tetra substituted halogenation products can be observed. Analysis of lab and pilot corrosion experiments by HPLC aligned the bromine product peaks to the assigned HPLC peaks from the NMR study, as well as the retention times of the synthetic mono-bromo standard. The HPLC results in Table 8 below show the distribution of brominated products for an example corrosion experiment with BMDZ, with the most abundant 5-Br and 5,6-diBr BMDZ labeled.

The reaction products of BMDZ under halogentation conditions included a BMDZ substituted in the 5 position: (5-bromo-1H-benzo[d]imidazol-2-yl)(phenyl)methanol (Br-BMDZ). Other reaction products included di-, tri-, and tetra-substituted BMDZ compounds.

TABLE 8

Distribution of brominated products (ppm)

| Sample ID | BMDZ | Br-BMDZ | diBr-BMDZ | triBr-BMDZ | tetraBr-BMDZ | Total |
|---|---|---|---|---|---|---|
| BMDZ Control | 3.4 | — | — | — | — | 3.4 |
| Experiment #1 | 0.2 | 1.4 | 1.0 | 0.2 | 0.1 | 2.9 |
| Experiment #2 | 0.2 | 1.6 | 1.1 | 0.2 | 0.1 | 3.2 |

When BMDZ is exposed to oxidizing chlorine, some chlorinated BMDZ is formed along with other oxidation byproducts. Table 9 shows the amount of byproducts formed from oxidizing BMDZ.

TABLE 9

Oxidation byproducts of BMDZ, such as Cl-BMDZ

| | Concentration (ppm) | | |
|---|---|---|---|
| Sample ID | BMDZ | Cl-BMDZ | Byproduct of oxidation | Total |
| Experiment #3 start | 5.0 | <0.1 | <0.1 | 5.0 |
| Experiment #3 end | 4.8 | <0.1 | 0.2 | 5.0 |
| Experiment #4 start | 5.4 | <0.1 | <0.1 | 5.4 |
| Experiment #4 end | 5.1 | <0.1 | 0.2 | 5.3 |

Example 6

The products identified during the in situ corrosion testing were synthesized ex-situ. Representative synthesis procedure to obtain halo-substituted BMDZ: A round bottom flask was charged with DL-Mandelic acid (0.05 mole) and 4-Bromo-1,2-diaminobenzene (0.05 mole) and about 30 g of 5 N Sulfuric acid. The reaction mixture was refluxed at about 100° C. for 8 hours. After completion, the final hot reaction mixture was carefully added into an ice-cold 10% NH₄OH solution. The resulting heterogeneous mixture was stirred for an additional 30 min at room temperature. The precipitate formed was filtered and the resultant solid was washed with water to obtain Br-BMDZ as brown color solid in about 80% yield. CI-BMDZ refers to Compound 3 in Table 1.

Compound structures and chemical names were prepared and determined using ChemDraw Professional version 15.1.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of reducing corrosion of a metal surface in an aqueous system, comprising:
adding to the aqueous system comprising the metal surface:

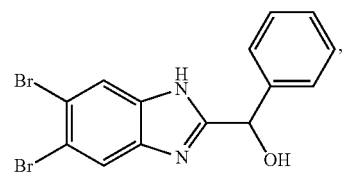
(Compound 1)

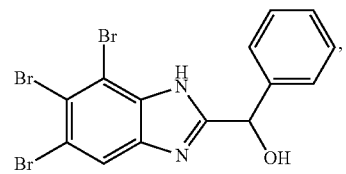
(Compound 2)

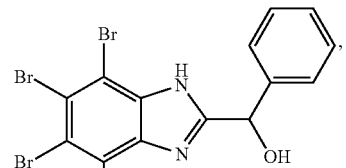
(Compound 3)

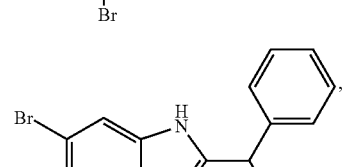
(Compound 4), and

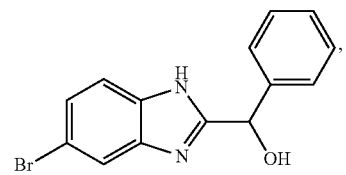
(Compound 5)

or salts thereof, wherein the Compound 1, the Compound 2, the Compound 3, the Compound 4, and the Compound 5 are added to the aqueous system in a ratio of 1.0:0.1:0.1:0.1:1.4.

2. The method of claim 1, further comprising adding a halogen stabilizer that is an isocyanate, a hydantoin, sulfamic acid, ammonia, urea, an amine, or any combination thereof.

3. The method of claim 1, further comprising measuring a corrosion rate of the metal surface in the aqueous system.

4. The method of claim 1, wherein the metal surface comprises copper or a copper alloy.

5. The method of claim 1, further comprising adjusting a dosage of the Compound 1, the Compound 2, the Compound 3, the Compound 4, and the Compound 5, or the salts thereof, to achieve a predetermined corrosion rate.

6. The method of claim 1, wherein a dosage of each of the Compound 1, the Compound 2, the Compound 3, the Compound 4, and the Compound 5 ranges from about 0.01 ppm to about 100 ppm.

7. The method of claim 1, wherein the aqueous system comprises a biocide.

8. The method of claim 1, wherein the aqueous system is chlorinated, brominated, iodated, or any combination thereof.

9. A composition, comprising:
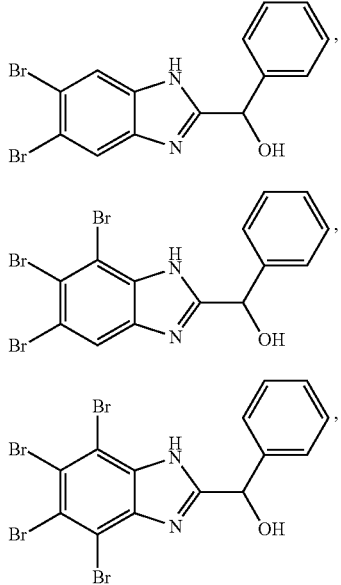
(Compound 1)
(Compound 2)
(Compound 3)
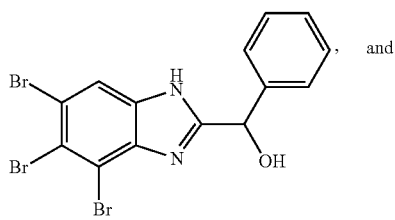
(Compound 4)
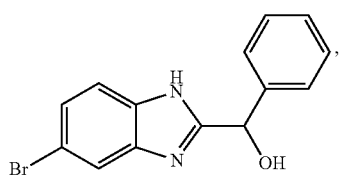
(Compound 5)
or salts thereof, wherein the Compound 1, the Compound 2, the Compound 3, the Compound 4, and the Compound 5 are present in the composition in a ratio of 1.0:0.1:0.1:0.1:1.4.
* * * * *